United States Patent [19]
Dante

[11] Patent Number: 5,856,332
[45] Date of Patent: Jan. 5, 1999

[54] COMPOSITION AND METHOD OF TREATING DEPRESSION USING A PENTACYCLIC NUCLEUS OPIOID ANTAGONIST IN COMBINATION WITH A TRICYCLIC ANTIDEPRESSANT

[75] Inventor: Lee G. Dante, Merion Station, Pa.

[73] Assignee: John S. Nagle, Esq., Thousand Oaks, Calif.

[21] Appl. No.: 755,795

[22] Filed: Aug. 28, 1996

Related U.S. Application Data

[62] Division of Ser. No. 560,820, Nov. 20, 1995, which is a division of Ser. No. 31,096, Mar. 2, 1993, Pat. No. 5,512, 593.

[51] Int. Cl.⁶ .......................... A61K 31/44; A61K 31/55; A61K 31/335; A61K 31/135
[52] U.S. Cl. .......................... 514/282; 514/217; 514/450; 514/654; 514/211
[58] Field of Search ...................................... 514/282, 217, 514/450, 654, 211

[56] References Cited

U.S. PATENT DOCUMENTS 5,064,834  11/1991  Zimmerman et al. .................. 514/279

OTHER PUBLICATIONS

Budavari, S., Ed., The Merck Index, p. 780, "imipramine", entry No. 4835, 1989.

*Primary Examiner*—William R. A. Jarvis
*Attorney, Agent, or Firm*—John S. Nagle, Esq.

[57] ABSTRACT

A new composition and method for treating depression is claimed comprising administering to a patient exhibiting said illness or illnesses a pharmacologically effective dose of an opioid antagonist having a pentacyclic nucleus, and a pharmacologically effective dose of a tricyclic antidepressant.

8 Claims, No Drawings

COMPOSITION AND METHOD OF TREATING DEPRESSION USING A PENTACYCLIC NUCLEUS OPIOID ANTAGONIST IN COMBINATION WITH A TRICYCLIC ANTIDEPRESSANT

This application is a divisional of Ser. No. 08/560,820, filed Nov. 20,1995, which is a divisional of Ser. No. 08/031,096, filed Mar. 2, 1993, now U.S. Pat. No. 5,512,593.

BACKGROUND OF THE INVENTION

1. Field of the Invention

The present invention relates to the use of an opioid antagonist such as naltrexone in combination with one or more serotonin (5-hydroxytryptamine or 5-HT) or norepinephrine reuptake inhibitor(s) and/or lithium to treat mental or emotional disorders characterized by depression, obsessiveness, depression with anxiety, mania, manic depression, depression with manic episodes, and depression concomitant with an illness causing seizures which are inhibited by carbamazepine, or a combination of any of these mental or emotional illnesses, or mental or emotional illnesses with seizures. The inventor has discovered that naltrexone is useful in combination with lithium and/or one or more serotonin (5-HT) uptake inhibitor and/or norepinephrine (N.E.) uptake inhibitor drug compounds in treating patients whose depression and/or associated mental illnesses or conditions were refractory to drug treatment using one or more known antidepressant agents or agents for manic and manic depressive disorders such as lithium, and tricyclic and a-typical antidepressants including, but not limited to clomipramine, amitriptyline, imipramine, sertraline and nortriptyline that inhibit 5-HT and/or N.E. reuptake.

The inventor has further discovered that such treatment using naltrexone in combination with lithium and/or 5-HT or N.E. reuptake inhibitors is effective even where benzodiazepines are concurrently administered to treat anxiety. Additionally, the inventor has discovered that lithium in combination with naltrexone in some cases reduces manic and manic depressive bipolar symptoms.

2. Description of the Related Prior Art

A general discussion of the effectiveness of tricyclic antidepressants and non-tricyclic a-typical antidepressants in inhibiting 5-HT and/or N.E. neuronal synaptic reuptake and in treating depression, along with the pharmacology of these compounds is found in Goodman and Gillman, *The Pharmacological Basis of Therapeutics*, 7th and 8th Eds. (MacMillan Publ. Co.) Chapt. 19, Section 11 "Drugs Used in the Treatment of Disorders of Mood", incorporated by reference herein. According to the present invention, tricyclic antidepressants include, but are not limited to, imipramine, amitriptyline, trimipramine, doxepin, desipramine, nortriptyline, protriptyline, amoxapine, clomipramine, maprotriline, and carbamazepine, and their pharmaceutically effective salts and esters, such as, but not limited to their hydrochlorides, maleates, tartrates and lactates. Although carbamazepine is approved in the U.S. as antiepileptic, it is chemically related to tricyclic antidepressants, its actions on human brain neurons are not completely known, and for the present invention it is classified as a tricyclic antidepressant. See, Goodman and Gillman, *The Pharmacological Basis of Therapeutics*, referenced above, 7th Ed., page 457 et seq.

According to the present invention, a-typical antidepressants include, but are not limited to, bupropion, sertraline, fluoxetine, and trazodone and their pharmacologically effective salts and esters, such as, but not limited to, their hydrochlorides, maleates, tartrates and lactates.

Additional discussion of these drug compounds and their analogs' pharmacologic action in inhibiting 5-HT and N.E. and in treating depression is found in the *Physician's Desk Reference* (PDR), 47th Ed., 1993, published by Medical Economics Co., Inc., Montvale, N.J., indexed by generic compound name and incorporated by reference herein.

The opioid antagonists which may be employed in the present invention have been known for use in treatment of opioid overdose and to prevent abuse of opioids such as heroin or morphine. The pharmacology of opioid antagonist compounds are described in Goodman and Gillman, *Pharmacological Basis of Therapeutics*, 7th & 8th Eds. (as noted above), Chapt. 22, "Opioid Antagonists", incorporated by reference herein, and include, but are not limited to cyclazocine, naloxone, opioid antagonist compounds having the same pentacyclic nucleus as nalmefene, naltrexone, nalmefene, nalorphine, nalbuphine, thebaine, levallorphan, pentazocine, oxymorphone, butorphanol, buprenorphine, levorphanol, meptazinol, dezocine, and pentazocine and their pharmacologically effective salts and esters such as, but not limited to their hydrochlorides, maleates, tartrates and lactates.

The generally accepted use for opioid antagonists in treatment of human ailments has been for reversing opioid toxicity and overdoes, and in preventing abuse of opioids, such as heroin and morphine. However, Glover, in U.S. Pat. No. 5,028,612 incorporated by reference herein, discusses use of opioid antagonists, such as naltrexone, in a method for treating emotional numbness where emotional numbness is "conceptualized as a biopsychological response to extreme emotional or physical trauma" and is featured by a person's subjective experience of inability to feel emotions, and lack of care and concern for others.

Glover also discloses that naltrexone may be used in treatment of emotional numbness coupled with other emotional disorders, such as post traumatic stress syndrome, schizophrenia, depression, anxiety, hypochondria, and psychomotor disorders, although no support for success in treating such patients is disclosed.

Horrobin in U.S. Pat. No. 4,388,324 discloses a method of moderating the effects of taking alcohol by administering, among other compositions, a composition of γ-linolenic acid and/or ascorbic acid and/or ethyl alcohol and/or opioid antagonist (See, col. 7, lines 30–35). Horrobin discloses that endogenous opioid excess, suspected in schizophrenia, coeliac diseases and psoriasis may be reversed by opioid antagonists such as naloxone (See, U.S. Pat. No. 4,388,32, col. 3, lines 15–19).

SUMMARY OF THE INVENTION

In many cases of profound depression, tricyclic and a-typical antidepressants and lithium do not provide sufficient relief to patients so as to prevent suicide ideation or allow the patient to successfully carry out continuous daily work routines and social routine activities. In some cases of endogenous depression, reactive depression, and in some cases where patients exhibit depression without suicide ideation, tricyclic and a-typical antidepressants and lithium do not satisfactorily control patient symptoms or condition.

It is an object of the present invention to provide a novel method for treating depression, obsessiveness, depression with obsessiveness, depression with anxiety, mania, depression associated with bipolar conditions such as manic depression, depression with manic episodes, and depression concomitant with an illness causing seizures which are inhibited by carbamazepine, or a combination of these mental or emotional illnesses. These mental or emotional illnesses to be treated may or may not be successfully treatable with a tricyclic or a-typical antidepressants or lithium or a benzodiazepine with anti-anxiety activity or a combination of these agents without concomitant opioid antagonist administration. The novel method of treatment is accomplished by adding an opioid antagonist drug compound to the drug treatment regimen for emotional or mental illness or emotional or mental illness concomitant with an illness causing seizures. Preferably, the opioid antagonist added to the treatment regimen is naltrexone (Trexan) given in an amount of 10–150 mg. per day, along with other medication for depression and/or manic or bipolar disorder.

It has further been determined that such a drug combination using an opioid antagonist or partial antagonist decreases the craving for sugars and carbohydrates often experienced with conventional tricyclic and a-typical antidepressant therapy.

The amounts of tricyclic or a-typical antidepressant or lithium which may be used with opioid antagonist to achieve the invention are dosage amounts typically given in treatment of depression, mania, or manic depression bipolar conditions well known to physicians treating mental or emotional conditions and to pharmacists, pharmacologists, and those skilled in the art, and further are those as directed by the labelling for these drugs as found in the 1993 PDR. The amount of opioid antagonist to be administered should be tailored to individual patient needs but generally is in the range of 10–150 mg/day. However, larger doses may be given if tolerated well by the patient, as needed. Appropriate and safe dosages for opioid antagonists are generally discussed in the PDR for each opioid antagonist and in Goodman and Gillman, *Pharmacological Basis of Therapeutics*, referenced above, and also may be determined on a molar weight basis equivalent to that for 10–150 mg. of naltraxone (Trexan).

The tricyclic antidepressants which may be used in the present invention include, but are not limited to, imipramine, amitriptyline, trimipramine, doxepin, desipramine, nortriptyline, protriptyline, amoxapine, clomipramine, maprotiline, and carbamazepine and their pharmaceutically effective salts and esters.

The a-typical antidepressants which may be used in the present invention include, but are not limited to, bupropion, sertraline, fluoxetine, trazodone, and their pharmacologically effective esters and salts.

The opioid antagonist which may be used in the present invention include, but are not limited to, naloxone, opioid antagonist having the same pentacyclic nucleus as nalmefene, naltrexone, nalmefene, nalorphine, nalbuphine, thebaine, levallorphan, oxymorphone, butorphanol, buprenorphine, levorphanol, meptazinol, pentazocine, dezocine, and their pharmacologically effective esters and salts.

The pentacyclic nucleus is exemplified in the structural formula for nalmefene shown below:

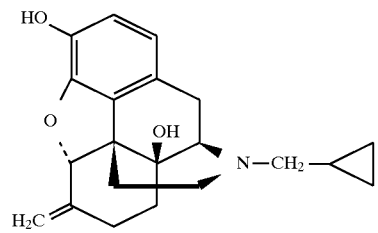

The opioid antagonist to be used in the invention may also possess some opioid agonist activity, and thus may be a partial antagonist with some agonist activity (partial agonist activity).

DETAILED DESCRIPTION OF PREFERRED EMBODIMENTS

The present invention relates to the use of opioid antagonists in combination with lithium and/or a tricyclic antidepressant and/or an a-typical antidepressant with and without concomitant administration of an anti-anxiety agent such as a benzodiazepine to treat emotional or mental illness or emotional or mental illness concomitant with an illness causing seizures.

It has been discovered that such a treatment results in remarkable alleviation of patients' suicide ideation and general depressed state or mania where such depressed or manic condition was refractive to treatment without opioid antagonist but with lithium and/or a tricyclic antidepressant and/or an a-typical antidepressant.

Preferably, in the present invention, the patient is given a dose of 25 or 50 mg. of Trexan per day in the morning, depending on the size of the patient and the severity of the symptoms of depression.

Some patients may experience several days of sleepiness when Trexan is used in combination with tricyclic or a-typical antidepressants and in these patients an alternative dose would be in the neighborhood of 10 mg taken at bedtime for the first three days of administration. On the fourth day, 10 mg may be administered and assuring that no sleepiness is evident the dose should be advanced to 25 mg. each morning for the next four weeks. In some individuals, especially those experiencing seasonal depressions, administration at night may be more effective and that effect would be noted within a few days of switching the time of administration following the first month of treatment. After one month of treatment, some individuals showing a response to the psychotropic medicine that is being given concurrently may get a response by increasing the dose of the opioid antagonist. In the case of Trexan, a dose of 50 mg. has been effective in getting response to develop.

A number of adverse effects of the administration of psychotropics have been observed to diminish upon this combination therapy, most notably the weight gain associated with long term administration of tricyclics. The effect of using opioid antagonists to augment treatment with psychotropic medications is not restricted to depressive disorders as attenuation of hostility and irritability by antidepressant medications has been enhanced as well as the reduction in anxiety states and obsessive compulsive states. The facilitation of effect is not restricted to those who are nonresponsive to psychotropic agents but has been observed in those who have had responses which, while satisfactory to the patient, were many times improved upon augmentation with the opioid antagonist.

The patients whose treatment with antidepressants are to be supplemented by benzodiazepine medication experience a dramatic decrease in their requirement for those categories of medication upon successful combination of the antidepressant being taken with naltrexone. In several cases studied, treatment with the opioid antagonist alone was completely unsatisfactory as was treatment with the psychotropic medication by itself. This phenomena has been noted with amitriptyline (Elavil), clomipramine (Anafranil), imipramine (Tofranil), and sertraline hydrochloride (Zoloft) and Lithium. Promising results have also been obtained with carbamazepine (Tegretal), bupropion (Wellbutrin), and fluoxetine (Prozac).

Patients should be warned about not stopping benzodiazepine medicines such as alprazolam (Xanax) or lorazepam (Ativan) without supervision otherwise their perception of not needing the effects of these anti-anxiety agents may lead them to stop too abruptly and precipitate withdrawal symptoms. Occasionally, in the first three to five days of administration, patients describe customarily pleasant dreams replaced by anxious or irritable dreams. This phenomena subsides after a few days.

The invention will be more fully understood by reference to the following examples.

EXAMPLE 1

A woman in her thirties who had a long history of depression treatment failure requested new treatment. She had, at various times, been bulimic, self-mutilating, alcoholic, and subject to obsessive thoughts. She had recurrent major depressive episodes which included characteristic vegetative signs of disturbed sleep, decreased appetite, energy, ability to concentrate and remember as well as the affective symptoms of sadness, irritability, and intense anxiety. At the time new treatment was begun, she presented symptoms of depression and insomnia. A variety of antidepressants were tried, the last being clomipramine hydrochloride (Anafranil), approved as an anti-obsessive drug in the U.S. but a quite effective antidepressant in use in other countries for many years. At a dose of 200 mg. Anafranil at bedtime, she got a very minimal lifting of depression but was able to sleep. Months later, she presented, having discontinued the Anafranil some time before but then noted a return of increased depression and insomnia.

Restarting the Anafranil improved her sleep but little else. Trexan was added at a dose of 50 mg. daily in the morning and from three to five weeks after beginning this regimen, she noted a dramatic lifting of the depression.

After a period on full doses of Anafranil, Anafranil was slowly withdrawn stopping at 50 mg. of the antidepressant at night. She had a moderate reduction in mood but insisted that she still had an impressive result compared to post-treatment.

The Trexan was given at night instead of in the morning and she experienced an immediate return of depression and of special note, a return of what she described as obsessive thoughts and behaviors. Reinstatement of the Trexan in the morning resulted in immediate return of the ameliorative effect on depression and the cessation of obsessive thinking.

The patient was returned to treatment with 150–200 mg. Anafranil at night and 50 mg. Trexan in the morning with good results.

EXAMPLE 2

An obese woman in her thirties who had been hospitalized for recurrent major depressive symptoms requested treatment. She also had vegetative signs and was frequently suicidal. She was treated with large doses of amitriptyline (Elavil), fluoxetine hydrochloride (Prozac) and eventually sertraline hydrochloride (Zoloft) with marginal effects. She then took a lethal overdose of amitriptyline which she surprisingly survived. During her last hospital stay, a stimulant, Ritalin, was added in doses up to 160 mg. daily because of her lifelong distractibility and school difficulties consistent with Attention Deficit Disorder. She felt markedly better on Ritalin plus Zoloft 150 mg. in the morning but still complained of craving for sweets, a frequent side effect of antidepressant therapy which in her case resulted in 100 lb., plus, weight gain. She was also taking substantial doses of alprazolom (Xanax). The combination allowed her to be out of a hospital and reasonably non-suicidal.

She was started on Trexan, 25 mg., in the morning without making any other changes. Very rapidly she lost her craving for sweets and a weight loss effort which was stalled took off. She lost thirty pounds in three weeks. After three weeks of Trexan augmentation she started to feel "Happy" and without prompting she discontinued all use of Xanax. The dosage of Ritalin was then reduced. While on combination therapy of Zoloft, Ritalin and Trexan, the patient has had no suicide ideation and continues to report being happy.

The loss of a carbohydrate craving is also of note as this is one of the most prominent causes of non-compliance in depressed patients. She was maintained with Zoloft, Ritalin, and Trexan 50 mg. dosing in the morning.

EXAMPLE 3

An obese man with a history of chronic recurrent depressive episodes especially characterized by explosive rage and a pervasive irritability requested treatment. He had racing thoughts and frequent swings in energy. In addition, he was subject to distractibility going back through early childhood. His diagnosis was Bipolar Mood Disorder, type 2. He responded to Amitriptyline 200 mg. at bedtime augmented by Lithium Carbonate up to 900 mg. daily. He was pleased with his result noting diminishing anger, better self control and was willing to live with the craving for sweets which treatment brought out despite gaining about 80 lbs. Then, 25–50 mg. of Trexan was added to his medicines taken in the morning and again after three to four weeks he noted a dramatically better mood.

He reported, "This is strange. All my life I've been suspicious and have looked at things expecting the worst. I have always been negative. Now I'm looking at things positively and it feels weird." He commented that he no longer craved sweets and reported losing about 10 lbs. a week. He said that his mood swings were gone and his anger was completely gone. This result was dramatically different than what was evident before the Trexan was added. He was then fired in a corporate downsizing and reported that he did not understand why he was just calmly going about the transition rather than falling apart.

EXAMPLE 4

A recovering alcoholic about age sixty with a major depression requested new treatment. He commented that he had not been happy for at least twenty five years. He was started on Zoloft, 50 mg. in the morning and 10, 50 mg. Trexan tablets with the instruction to take 25 mg. each morning until he ran out. He had been taking lorazepam (Ativan) 0.5 mg. four times a day for some time and was anxious that it be continued. After three weeks, he reported that the "Zoloft" was working and elected to stop taking the Trexan since he "couldn't feel it do anything". He said he was feeling happy for the first time and that on his own he had stopped taking the Ativan except occasionally at night. One month later, he was not feeling quite as well and had resumed the full dose of Ativan.

He was instructed that he may have responded better to the Zoloft earlier because of the concurrent use of Trexan and he consented to restart it. One month later he reported his depression was gone, and had again, without prompting, discontinued the use of Ativan.

EXAMPLE 5

A chronically depressed, agoraphobic woman requested treatment for relief from severe suicidal depressive episodes. Due to her prominent phobic symptoms, she was started on imipramine 150–300 mg. at bedtime with equivocal results. A shift to Anafranil at similar doses resulted in a significantly better lifting of her mood but she was still quite impaired and subject to mood swings. One weekend she called and requested hospitalization due to very urgent wishes to kill herself. She happened to mention that Darvon would usually stop the urge to kill herself and rather than put her in hospital, she was given Darvon temporarily.

She was then started on Trexan 25 mg. in the morning with imipramine and three weeks later she felt "cured". Because of her concern about expense, she stopped the Trexan without telling her physician and presented again a few weeks later in a markedly depressed state despite continuing the imipramine. She was instructed to restart the Trexan and after several weeks she had an enormously improved mood and a marked reduction in her agoraphobic symptoms. In this lady, concurrent antidepressant with naltrexone was necessary to prevent likelihood of losing the patient to suicide or a return of severe depression.

EXAMPLE 6

A fifty-some year old man with recurrent episodes of depression and explosive rage was being treated with imipramine for some three months prior to being admitted to the hospital. He was already. tying the rope around his neck when the police grabbed him. Three weeks after adding Trexan at 25 mg. in the morning to imipramine 175 mg. at bedtime, he began to describe a lifting of his depression and irritability and became quite social and lively.

EXAMPLE 7

A woman in her mid-thirties who had a leaking aneurysm requiring destructive brain surgery and relearning to speak, was treated. She had a lifelong history of depression and had been deeply depressed when seen. Treatment with 175 mg. of nortriptyline (Pamelor) for many months had resulted in equivocal improvement. After four weeks of Trexan 25 mg. in the morning with Pamelor, she began a marked and sustained remission of depression described by the patient as the best ever.

EXAMPLE 8

An operating room nurse with a bipolar depression which resisted tricyclics, a-typical antidepressants, and lithium, alone, requested treatment. She was taking 600 mg. of Tegretal at bedtime when started on Trexan and was only taking the Tegretal to sleep. She had no antidepressant effect. She was then started on 50 mg. of Trexan with Tegretal and she slept for three days. She was instructed to dissolve the Trexan in water and take gradually increasing doses beginning with less than 2 mg. per day. She was able to increase to 25 mg. daily and after several months became almost hypomanic, requiring periodic discontinuation of the Trexan to avoid becoming giddy on the job. She reported that it was the first medicine combination she had taken that improved her mood reliably.

Tegretal is a tricyclic but an anticonvulsant/antimanic rather than antidepressant.

EXAMPLE 9

It is expected that the patient of Example 8, above, would improve even further if her treatment with Tegretal plus Trexan (25 mg.) was supplemented or replaced with treatment administering lithium plus 25 mg. Trexan. This latter combination would solve her problems dosing herself with Tegretal and Trexan intermittently to correct her excess giddiness or mania, while preventing depressive episodes.

What is claimed is:

1. A method of treating depression comprising administering to a patient a pharmacologically effective dose of an opioid antagonist having a pentacyclic nucleus structurally analogous to naloxone, naltrexone, and nalmafene, and a pharmacologically effective dose of at least one tricyclic antidepressant.

2. The method of claim 1, wherein the pharmacologically effective dose of said opioid antagonist is 25 mg. for naloxone and a molar equivalent weight to 25 mg. of naloxone for opioid antagonists other than naloxone.

3. The method of claim 1, wherein the pharmacologically effective dose of said opioid antagonist is 50 mg. for naloxone and a molar equivalent weight to 50 mg. of naloxone for opioid antagonists other than naloxone.

4. The method of claim 1, wherein the pharmacologically effective dose of said opioid antagonist, administered orally is 10 mg. at bedtime for the first three days of treatment, 10 mg. in the morning on the fourth day of treatment, and thereafter when no daytime sleepiness if evident, 25 mg.

5. The method of claim 1, wherein said opioid antagonist or a pharmaceutically acceptable ester or salt thereof is administered in combination with a pharmaceutically acceptable carrier.

6. A composition for treating depression comprising a pharmacologically effective dose of an opioid antagonist having a pentacyclic nucleus structurally analogous to naloxone, naltrexone, and nalmafene, and a pharmacologically effective dose of at least one tricyclic antidepressant.

7. The composition of claim 6, wherein the tricyclic antidepressant is selected from the group consisting of imipramine, amitriptyline, trimipramine, doxepin, desipramine, nortriptyline, protriptyline, amoxapine, clomipramine, maprotiline, and carbamazepine and a pharmacologically effective salt or ester thereof.

8. The composition of claim 6, wherein the opioid antagonist is combined with a pharmaceutically acceptable carrier.

* * * * *